(12) United States Patent
D'Auria

(10) Patent No.: US 7,128,925 B2
(45) Date of Patent: Oct. 31, 2006

(54) DEVICE FOR APPLYING ACTIVE PRINCIPLES FOR PHARMACEUTICAL OR COSMETIC PURPOSES

(75) Inventor: Stanislas Boulet D'Auria, Cap D'Ail (FR)

(73) Assignees: 3X Engineering, Monaco (MC); Submin Limited, Dublin (IE)

(*) Notice: Subject to any disclaimer, the term of this patent is extended or adjusted under 35 U.S.C. 154(b) by 433 days.

(21) Appl. No.: 10/203,033

(22) PCT Filed: Feb. 2, 2001

(86) PCT No.: PCT/FR01/00319

§ 371 (c)(1),
(2), (4) Date: Oct. 15, 2002

(87) PCT Pub. No.: WO01/56540

PCT Pub. Date: Aug. 9, 2001

(65) Prior Publication Data

US 2004/0050402 A1    Mar. 18, 2004

(30) Foreign Application Priority Data

Feb. 4, 2000    (FR) .................................. 00 01621

(51) Int. Cl.
*A61K 9/00*    (2006.01)
*A61K 6/00*    (2006.01)
*A61K 8/02*    (2006.01)
*A61K 9/48*    (2006.01)
*A61J 1/00*    (2006.01)

(52) U.S. Cl. .................. 424/401; 424/451; 401/132; 132/317

(58) Field of Classification Search ................ 424/451, 424/489

See application file for complete search history.

(56) References Cited

U.S. PATENT DOCUMENTS 3,918,452 A    11/1975    Cornfield ................... 128/270
4,828,542 A *   5/1989    Hermann ...................... 604/3
6,508,604 B1 *  1/2003    Bechmann et al. ......... 401/132

FOREIGN PATENT DOCUMENTS

| DE | 34 37 833 | 7/1986 |
| FR | 2 754 450 | 4/1998 |
| GB | 1 304 375 | 1/1973 |
| JP | 63-178178 | 7/1988 |

* cited by examiner

Primary Examiner—Michael P. Woodward
Assistant Examiner—David Vanik
(74) Attorney, Agent, or Firm—James C. Lydon

(57) ABSTRACT

Device for applying at least one active principle, consisting of a material wherein one or several capsules or microcapsules containing the active principle(s) are distributed in a binder having a sponge-like consistency so that the active principle(s) is/are released when pressure is exerted on the material. The device consists of a first part (10) and a second part (12), separated by a tear-off portion (14), the capsule or most of the capsules or microcapsules being located in the first part close to the tear-off portion, the first part being detached from the second part by tearing the tear-off portion so as to obtain, at the breakage interface, a surface for applying the active principle(s) contained in the first part when pressure is exerted thereon.

6 Claims, 1 Drawing Sheet

DEVICE FOR APPLYING ACTIVE PRINCIPLES FOR PHARMACEUTICAL OR COSMETIC PURPOSES

TECHNICAL FIELD

This invention relates to devices consisting of a material to carry capsules or microcapsules containing one or more active principles which need to be protected from exposure to air before use, and in particular concerns a device for applying active principles which is produced from a material of this type commonly used in pharmaceutical and cosmetic applications.

BACKGROUND ART

In the cosmetic and pharmaceutical fields, many liquid products are sold in bottles. As soon as the bottle is opened for first-time use, contact with air inevitably entails oxidation which is detrimental to the product in the bottle. As a result, it is often impossible to go on using the product which has lost a part of its properties relatively quickly.

Other products are sold on some form of substrate, e.g. pads which have been pre-impregnated with toilet water or perfume. Once the packaging is broached, such substrates tend to dry out very quickly as well as providing a propitious medium for bacterial growth. The same disadvantages apply to make-up-removal wipes soaked in cleansing milk.

In consequence, using microcapsules was considered. Microcapsule technology is well known in the biomedical field. Microcapsules are spherical particles consisting of a solid envelope containing a liquid, solid or semi-solid principle.

Each microcapsule has diameter of between 50 μm and 1.5 mm and therefore actually constitutes a reservoir. The first industrial application for microcapsules was in the production of carbonless copy paper since which time this technology has been applied to resolve many problems in pharmacy. In practice, because their external covering inhibits exchange with the outside environment, microcapsules protect medicinal products from diverse chemical and physical phenomena such as humidity, heat and oxidation. Moreover, the rate at which active principles are released from microcapsules can be controlled and their bioavailability can be thus modulated. This can be achieved by varying a large number of different technical parameters, including the nature of the material used to produce the envelope, the relative proportions of the active principles, particle size, and the thickness of the envelope.

The above-mentioned properties have been exploited to produce a substrate acting as a medium for microcapsules, described for example in document FR-A-2.754.450. The material used is a foam such as a polyurethane foam, a polyethylene foam or any other polymer with a sponge-like consistency. The polyurethane foam, for example, is produced in a conventional process by condensation of a mixture of a polyol and isocyanate in the presence of water which leads to the release of carbon dioxide and therefore the formation of multiple cells which give the final polymer a sponge-like structure. The microcapsules are added to the above-mentioned three reagents and everything is thoroughly mixed together. When polymerization is complete, the resultant product is a sponge-like material with microcapsules distributed in the body of the foam which acts as a binder.

One of the characteristics of the material of the invention is that the cells communicate with one another so any products contained in the microcapsules can flow through the material when it is being used. It is important to include enough water in the reaction to induce the formation of open cells (i.e. inter-communicating cells). The ideal is of course to have a material in which 100% of the cells are open, but the above-mentioned applications are possible with a material in which only 60% of the cells are open. In practice, in addition to diffusion via the internal spaces of the cells, the products also diffuse as a result of impregnation of the material and capillary action. Application of a product contained in the microcapsules described in this document is achieved by exerting pressure on the substrate material in such a way as to burst the microcapsules to release the active principle(s) that they contain, so that these principles can reach the surface of the material by diffusion through the open cells.

However, using a substrate material such as is described in document FR-A-2.754.450 is associated with one major drawback. This is that the application surface can become contaminated with unwanted bodies such as dirt, dust or microorganisms, even if the material is sealed in packaging materials up till use. As a result, the active principles can become contaminated when they are released at the surface of the material so that topical application can lead to contamination of the skin and pathological consequences.

SUMMARY OF THE INVENTION

This is why the purpose of the invention is to provide a device for applying active principles contained in capsules or microcapsules distributed in a sponge-like material, within which the active principles are maintained perfectly sterile by virtue of the fact that the surface of application does not exist until the device is actually used.

The object of the invention is therefore a device for applying at least one active principle, consisting of a material in which one or more capsules or microcapsules containing the active principle(s) are distributed in a binder with a sponge-like consistency in such a way that the active principle(s) are released when pressure is exerted on the material. The device consists of a first part and a second part, separated by a tear-off portion, the capsule or most of the capsules or microcapsules being located in the first part close to the tear-off portion, the first part being detached from the second part by tearing the tear-off portion so as to obtain, at the breakage interface, a surface for applying the active principle(s) contained in the first part when pressure is exerted thereon.

BRIEF DESCRIPTION OF THE DRAWINGS

The purposes, objects and other characteristics of the invention will become more apparent in the light of the following description in which.

DETAILED DESCRIPTION OF THE INVENTION

Figure 1:
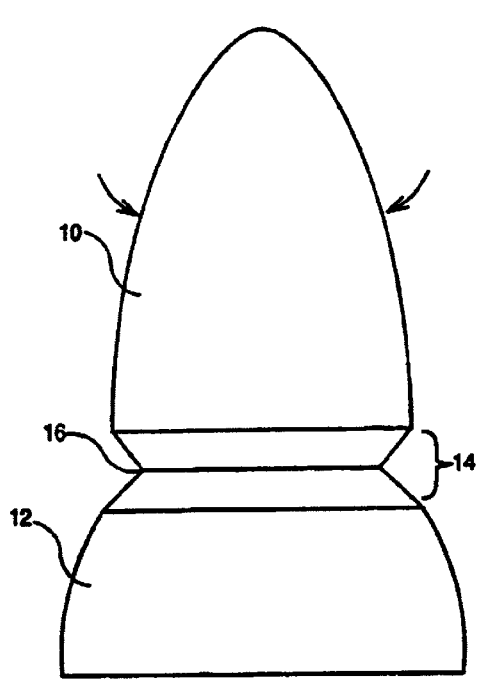
FIG. 1 shows a preferred embodiment of the device according to the invention.

According to a preferred embodiment illustrated in FIG. 1, the device consists of two parts 10 and 12 which can be easily separated by means of the tear-off portion 14. This portion is formed by a tapering of each of the two parts 10 and 12 to give a truncated cone-shape with a conical angle of about 45°, thereby giving rise to a tapered joint 16 where the two truncated cones meet. The tapering makes it easier to separate the two parts 10 and 12, separation being further facilitated by the breakage initiation provided by the angular configuration at the tear-off portion. In order to break the device open, one part 12 is held in one hand and the other part 10 is grasped at the points marked with arrows; a couple then exerted on the first part 10 will induce breakage at the joint 16.

The device according to the invention consists of a sponge-like material (e.g. foam) containing a high proportion of open cells. This foam can be generated by any means, notably polymerization, e.g. a polyurethane foam, or any other foam with a sponge-like consistency. Since the device is designed to be disposed of after a single use, the material chosen would preferably be biodegradable.

Figure 2:
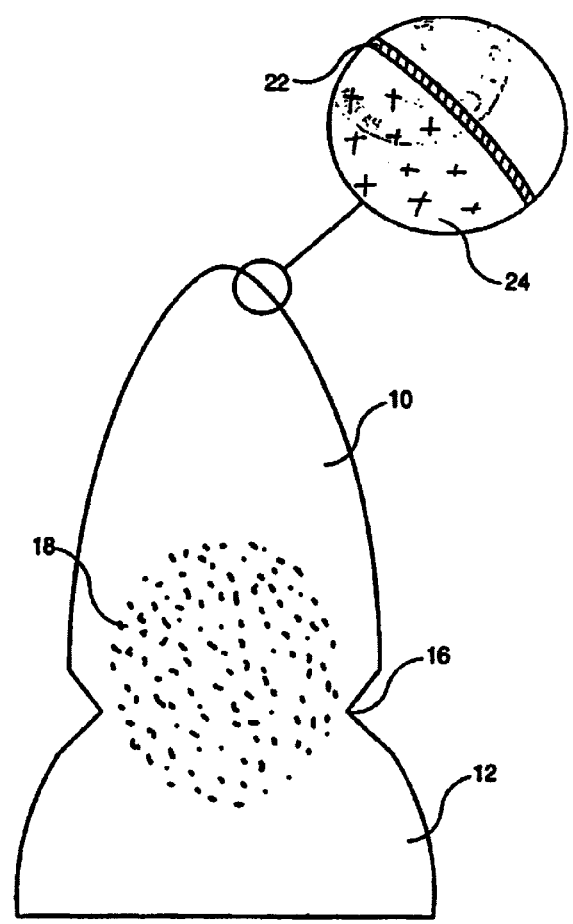
FIG. 2 shows a cross section through the device illustrated in FIG. 1, and also an enlarged insert showing the skin formed after formation of the sponge-like material.

As shown in FIG. 2, which is a cross section of the device as shown in FIG. 1, the microcapsules 18 are concentrated primarily in the area around the tear-off portion, i.e. close to the tapered joint 16. The microcapsules may vary in size, e.g. their diameter might be anywhere between 50 μm and 1.5 mm. However, capsules (rather than microcapsules) with a diameter of several millimeters could be used without departing from the scope of the invention.

Figure 3:
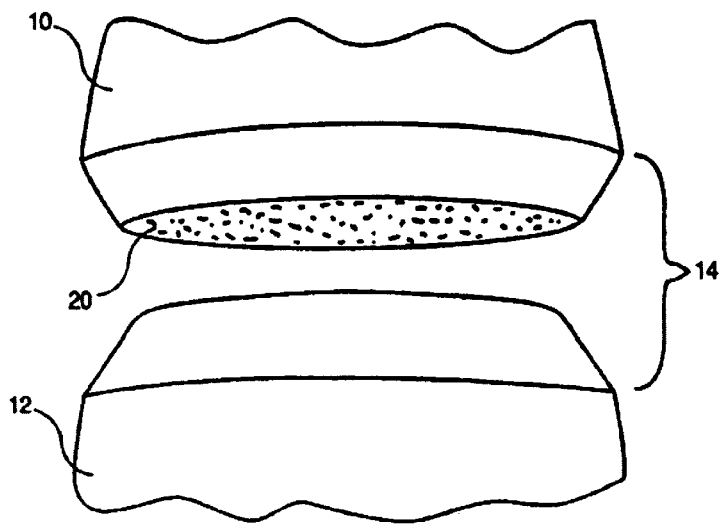
FIG. 3 is an enlarged view of the tear-off portion after the device illustrated in FIGS. 1 and 2 has been separated into two parts according to the principles of the invention.

FIG. 3 shows what the tear-off portion 14 looks like after the two parts 10 and 12 have been separated from one another: after breakage along the tapered joint 16, the upper part 10 carries an application surface 20, immediately around which the majority of the capsules or microcapsules are concentrated. A significant advantage of the invention is that-this surface is perfectly sterile insofar as it has never been in contact with any foreign body. The user can then release the active principle(s) from the application surface 20 by exerting pressure on part 10, e.g. by pressing with the thumb and index finger at the points indicated by arrows in FIG. 1.

One characteristic of the invention is that the microcapsules (or capsules) are as concentrated as possible close to the tear-off portion 14. In the case of the material being a form of polyurethane foam, this is achieved by first injecting the ingredients of the foam into the mold prior to polymerization, then adding the capsules or microcapsules, and finally the polymerization products again. During polymerization (which lasts a few seconds), expansion occurs and the microcapsules spread out into the area which will ultimately be close to the tearoff portion. In such a way that the microcapsules are evenly distributed through the foam, it is possible to vary the foaming time or alternatively to generate an extremely fluid foam or subject the mold to vibration.

It has been observed that, in certain conditions, the polymerization process in which liquid compounds are converted into a solid foam is associated with the formation of a skin 22 at the surface of the foam 24 as illustrated in FIG. 2. The advantage of this type of skin is not only that it protects the device from contamination from outside but it also protects the user's fingers when applying pressure to release the active principle(s).

Application devices or applicators according to the invention can be of any shape as long as they include a tear-off portion, close to which the capsules or microcapsules are relatively highly concentrated. Similarly, the device might consist of two different parts, each designed to serve as an applicator for a different active principle. In this case, breakage at the tapered joint 16 would generate application surfaces for two applicators after separation. In a special case, the device consists of two identical parts, both identical to part 10 of the device illustrated in FIG. 1, so that separation yields two identical applicators. The overall shape can be designed for an esthetic effect, or with ergonomic considerations so that picking up the applicator automatically leads to the crushing of the microcapsules in the tear-off portion.

There are many possible applications of the device according to the invention, mainly in the pharmaceutical and cosmetic fields. Thus, the microcapsules could contain a skin cleansing product, a liquid soap, a drug designed for topical application, a fragrance, a make-up removal product or some other kind of toiletry product.

A particular embodiment consists in sticking together a series of devices like that illustrated in FIG. 1 onto a vertical carrier. Thus, whenever the user needs a ready-to-use, sterile applicator, he or she can just pull one off with one hand until all the devices on the carrier have been used up.

It is clear that the device according to the invention can be used in any application which requires that the product to be applied not be released before the moment of use, release being achieved by the crushing of capsules or microcapsules. It should be noted that neither the number nor the size of the capsules or microcapsules is fixed: the number of capsules in the tear-off part could be small, ultimately just a single, large capsule (e.g. with a diameter of 5 mm) close to the application surface which is crushed to release the active principle at the moment when pressure is exerted by the user.

Finally, applications could be considered in which different kinds of capsule or microcapsule contain different products which react with one another at the moment of release to form one or more active principles.

The invention claimed is:

1. A device for applying at least one active principle, comprising a material wherein one or several capsules containing the active principle(s) are distributed in a binder having a sponge-like consistency so that the active principle(s) is/are released when pressure is exerted on the said material, said device comprising a first part and a second part, separated by a tearoff portion, the capsule or most of the capsules being located in said first part close to said tear-off portion, said first part being detached from said second part by tearing said tear-off portion so as to obtain, at the breakage interface, a first surface for applying the active principle(s) contained in the first part when pressure is exerted thereon and a second surface for applying the active principle(s) contained in the second part when pressure is exerted thereon, wherein said tear-off portion is formed by two truncated cones which meet at a tapered joint where breakage results in separation of said first part from said second part.

2. The device according to claim 1, wherein said tapered joint generates, after breakage, said first and second surfaces for applying the active principle(s).

3. The device according to claim 1 wherein said first part and said second part are symmetrical about the tapered joint.

4. The device of claim 1, wherein said tear-off portion contains microcapsules with a diameter of between 50 μm and 1.5 mm.

5. The device according to claim 4, wherein said microcapsules contain different products which react with one another to form active principle(s) when pressure is exerted on said material.

6. A method for dispensing a fragrance, comprising
providing the device of claim 1 wherein a fragrance is contained in the capsule(s);
tearing the tear-off portion of the device to obtain a breakage interface having two surfaces for applying the fragrance when a pressure is applied to said microparticles.

* * * * *